(12) United States Patent
Fong et al.

(10) Patent No.: US 7,626,004 B2
(45) Date of Patent: *Dec. 1, 2009

(54) PROTEIN PURIFICATION

(75) Inventors: Robin Fong, Mountain View, CA (US); Meng H. Heng, Belmont, CA (US)

(73) Assignee: Genencor International, Inc., Palo Alto, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 11/717,510

(22) Filed: Mar. 13, 2007

(65) Prior Publication Data

US 2007/0191594 A1 Aug. 16, 2007

Related U.S. Application Data

(63) Continuation of application No. 10/663,483, filed on Sep. 15, 2003, now Pat. No. 7,208,585.

(60) Provisional application No. 60/411,540, filed on Sep. 18, 2002, provisional application No. 60/411,537, filed on Sep. 18, 2002.

(51) Int. Cl.
*C07K 1/16* (2006.01)
(52) U.S. Cl. .................. 530/417; 435/183; 530/387.1
(58) Field of Classification Search .................. None
See application file for complete search history.

(56) References Cited

U.S. PATENT DOCUMENTS

| | | | |
|---|---|---|---|
| 5,411,873 A | 5/1995 | Adams et al. | |
| 5,429,950 A | 7/1995 | Power et al. | |
| 5,652,348 A | 7/1997 | Burton et al. | |
| 5,679,543 A | 10/1997 | Lawlis | |
| 6,255,115 B1 | 7/2001 | Beijersbergen et al. | |
| 7,208,585 B2 * | 4/2007 | Fong et al. | 530/417 |
| 2003/0229212 A1 | 12/2003 | Fahrner et al. | |
| 2004/0018573 A1 | 1/2004 | Power et al. | |

OTHER PUBLICATIONS

U.S. Appl. No. 60/373,889, filed Apr. 18, 2002, Power, et al.
U.S. Appl. No. 60/411,540, filed Sep. 18, 2002, Wang, et al.
*Harkki et al,, BioTechnology, 7:596-603, 1989.
*Mellor et al., Gene,24:1-14, 1983.
*Penttilâ et al., Gene 61:155-164, 1987.
*Sibakov.et al., Eur. J. Biochem., 145:567-572, 1984.
*Ward, Proc, Embo-Alko Workshop on Molecular Biology of Filamentous Fungi, Helsinki, pp. 119.128, 1989.

(Continued)

*Primary Examiner*—Jeffrey E Russel
(74) *Attorney, Agent, or Firm*—Danisco US Inc.

(57) ABSTRACT

The present invention relates to a method of purifying a protein of interest from its fusion analog, comprising obtaining a protein solution comprising a protein of interest and its fusion analog; adjusting the pH and/or ionic strength of the protein solution with an appropriate buffer for use with a Hydrophobic Charge Induction Chromatography (HCIC) resin, contacting the protein solution and HCIC resin column to allow binding of the protein of interest and its fusion analog, washing the resin and eluting the protein of interest from the resin by a pH gradient; wherein the protein of interest is substantially free of its fusion analog.

26 Claims, 14 Drawing Sheets

OTHER PUBLICATIONS

Guerrier, L. et al., "New method for the selective capture of antibodies under physiological conditions", *Bioseparation*, 9:211-221, 2000.

Guerrier, L. et al., "A Dual Mode Approach to the Selective Separation of Antibodies and Their Fragments", *Journal of Chromatography B*, 755:37-46, 2001.

Harkki, A., et al, "A Novel Fungal Expression System: Secretion of Active Calf Chymosin from the Filamentous Fungus *Trichoderma reesei*", *BioTechnology*, 7:596-603, 1989.

Iordanescu, S., "Recombinant Plasmid Obtained from Two Different, Compatible Staphylococcal Plasmids", *J. Bacteriol*, 597-601, 1975, vol. 124.

Mellor, J. et al., "Efficient Synthesis of Enzymatically Active Calf Chymosin in *Saccharomyces cerevisiae*", *Gene*, 24:1-14, 1983.

Penttilä, M. et al., "A Versatile Transformation System for the Cellulolytic Filamentous Fungus *Trichoderma reesei*", *Gene* 61:155-164, 1987.

Sibakov, M. et al., "Isolation and the 5'-end nucleotide sequence of *Bacillus licheniformis* α-amylase gene", *Eur. J. Biochem.*, 145:567-572, 1984.

Ward, M., "Heterologous Gene Expression in *Aspergillus*", *Proceedings of the EMBO-Alko Workshop on Molecular Biology of Filamentous Fungi*, Helsinki, pp. 119-128, 1989.

Nickerson, Kenneth W. and Bulla, Lee A., Jr., "Lipid Metabolism During Bacterial Growth, Sporulation, and Germination: an Obligate Nutritional Requirement in *Bacillus thuringiensis* for Compounds That Stimulate Fatty Acid Synthesis," *Journal of Bacteriology*, 123(2):598-603 (1975).

* cited by examiner

General Schematic of Antibody Structure
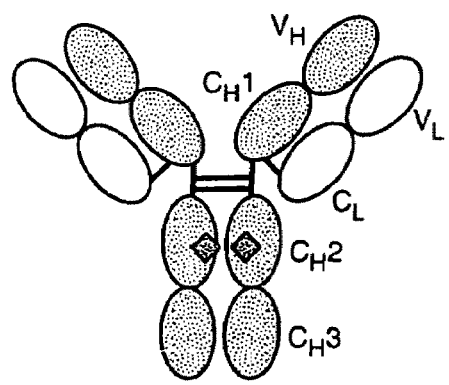
FIG._1A
General Schematic of Antibody Fragments
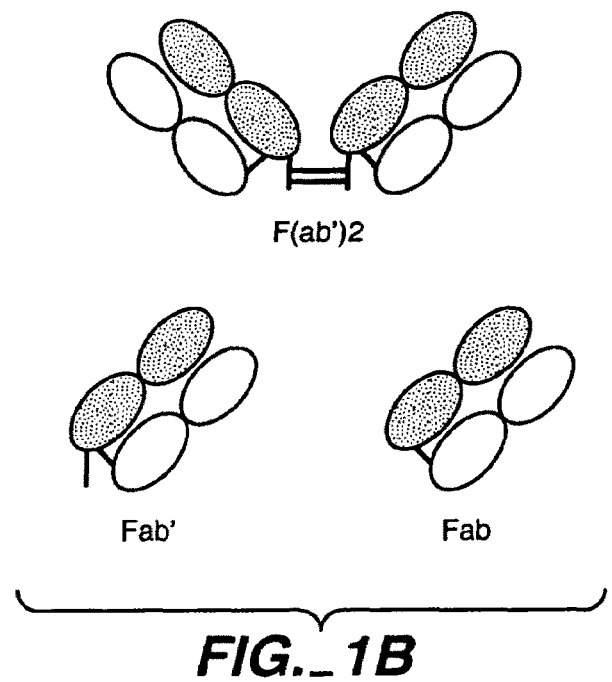
FIG._1B

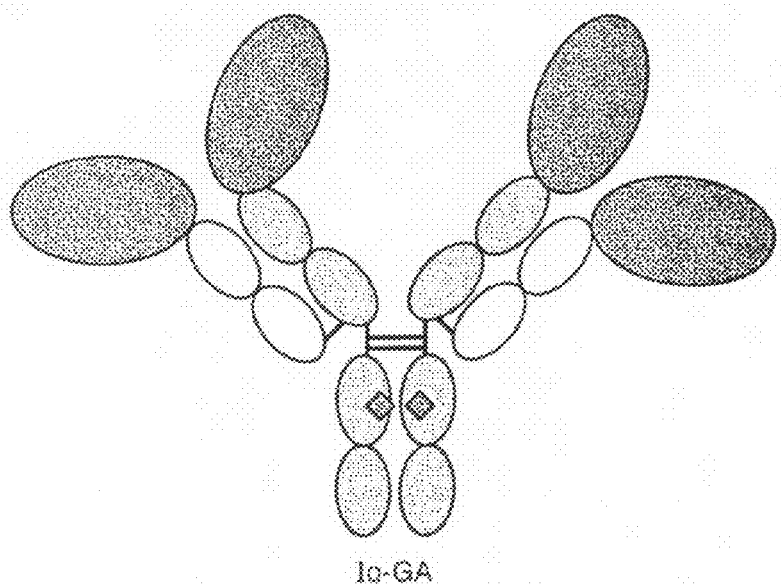
General Schematic of Antibody-Glucoamylase Fusion
Ig-GA
FIG._1C
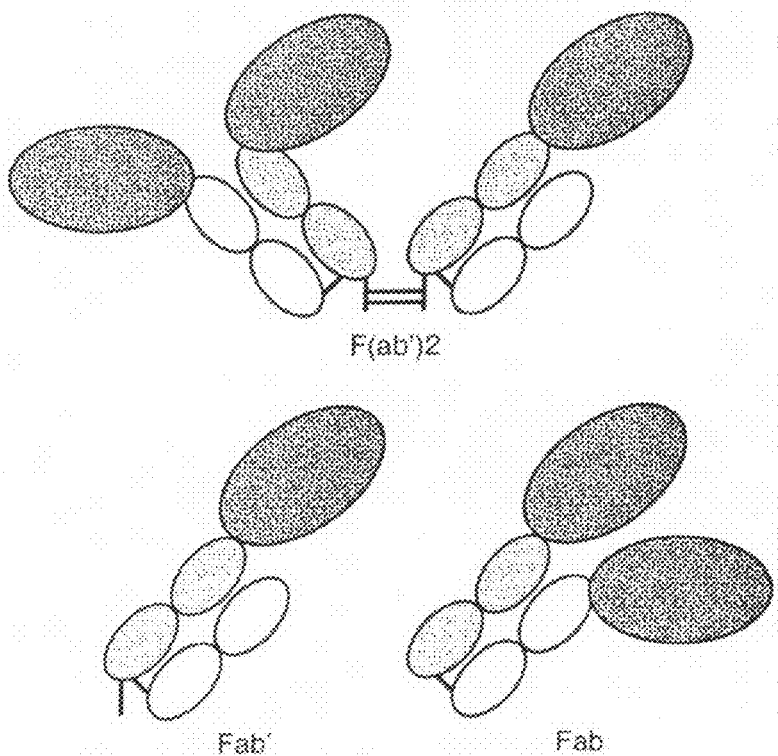
General Schematic of Antibody Fragment-Glucoamylase Fusions
F(ab')2
Fab'    Fab
FIG._1D

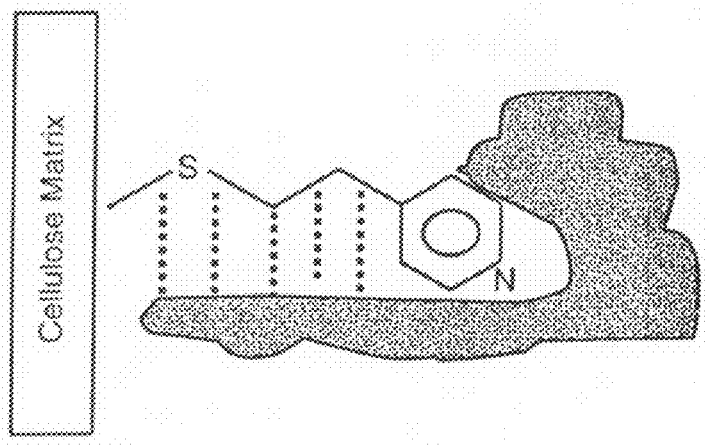
FIG._2A
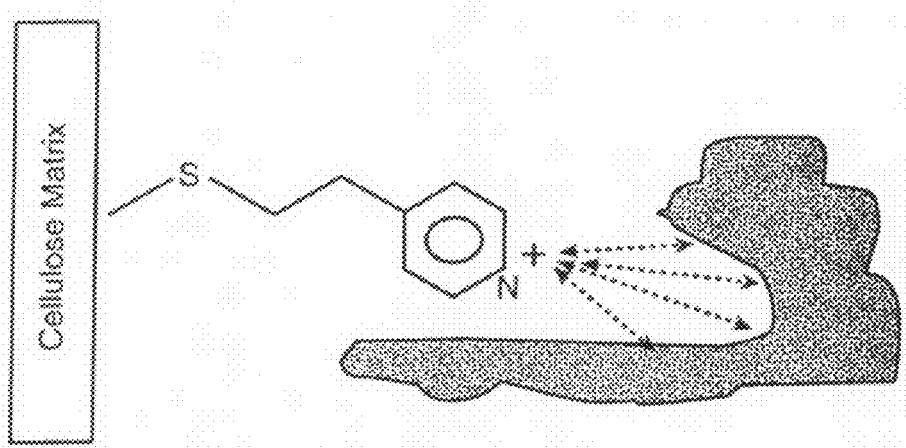
FIG._2B

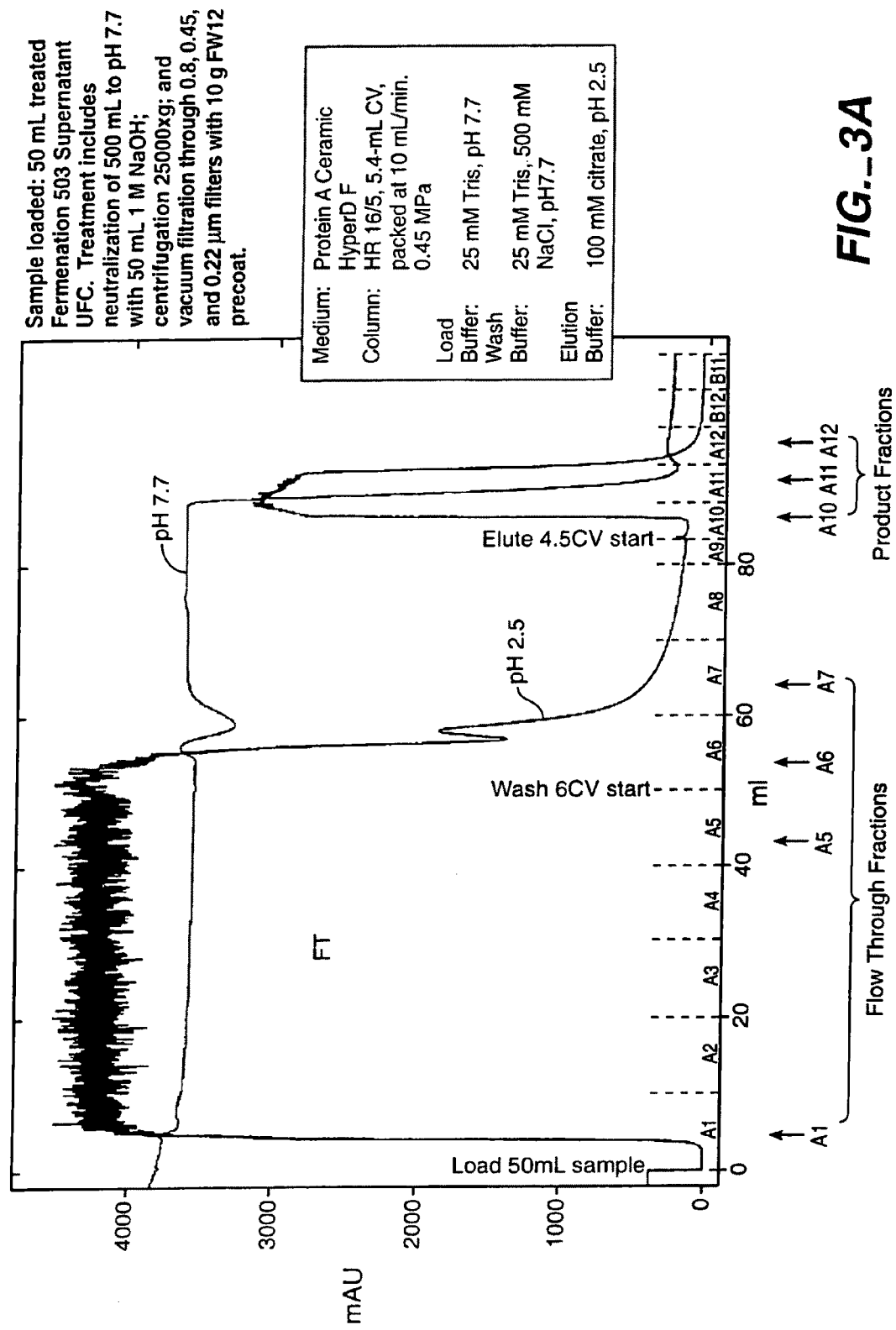
FIG._3A

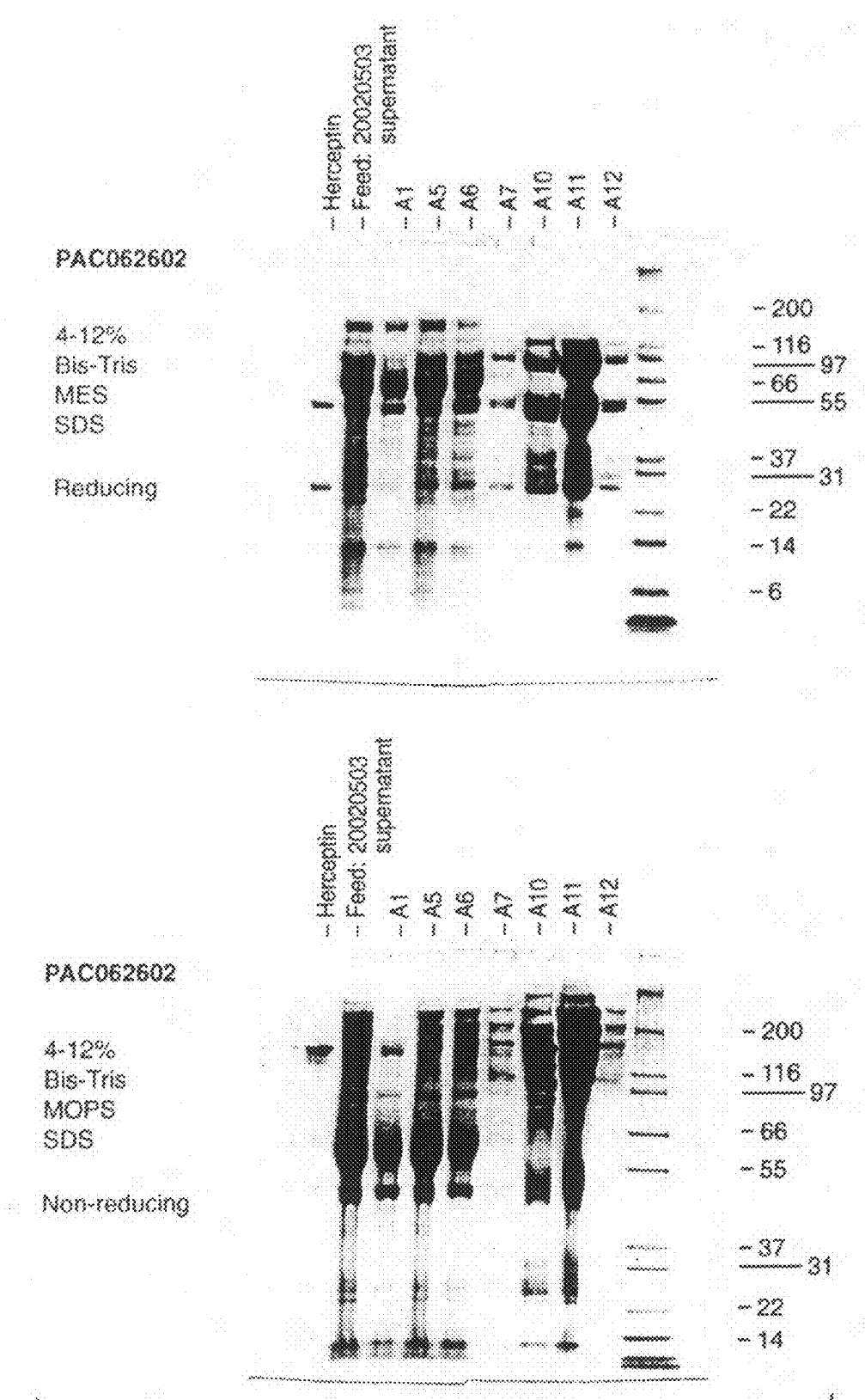
FIG._3B

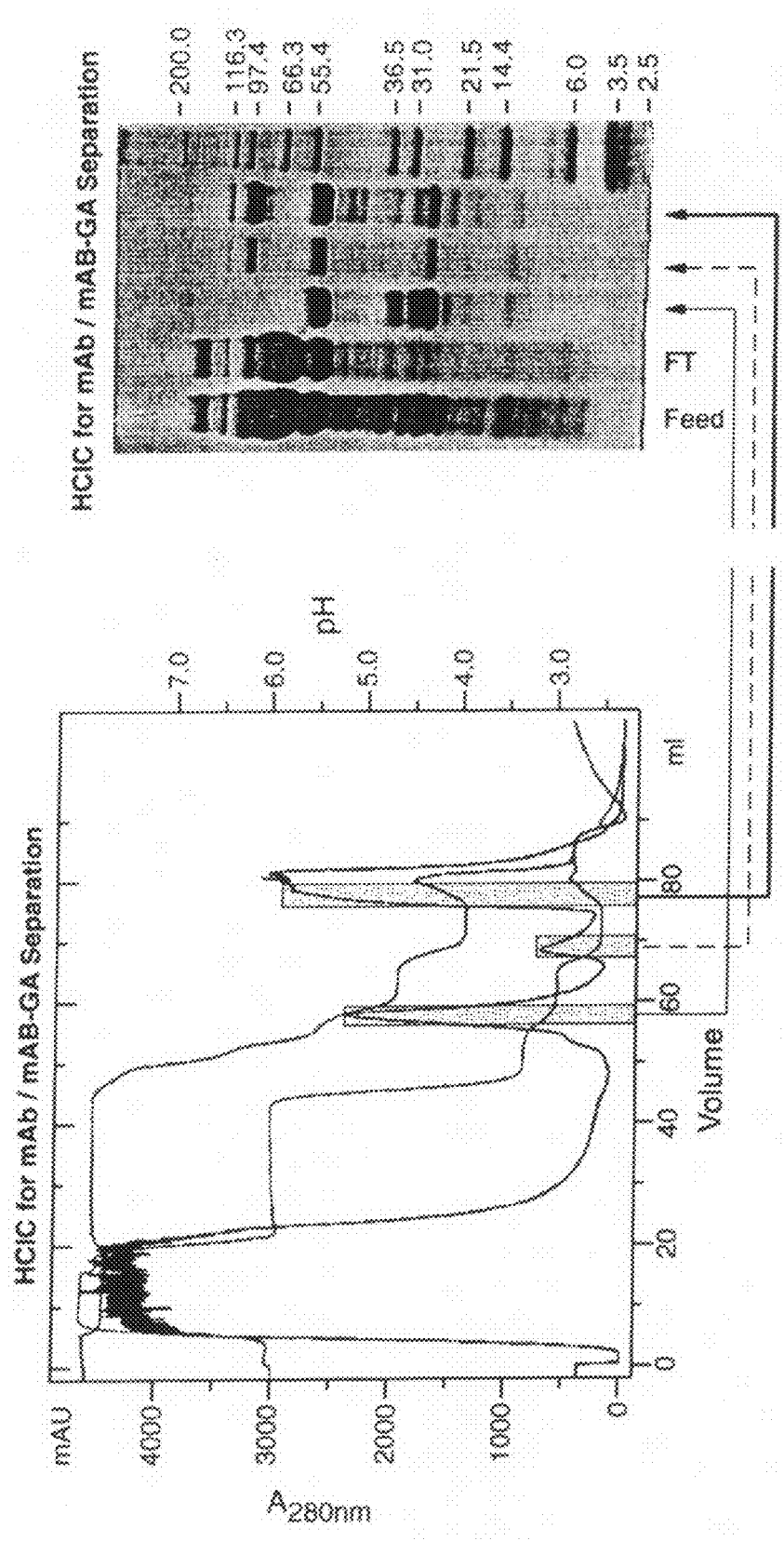
FIG._4B
FIG._4A

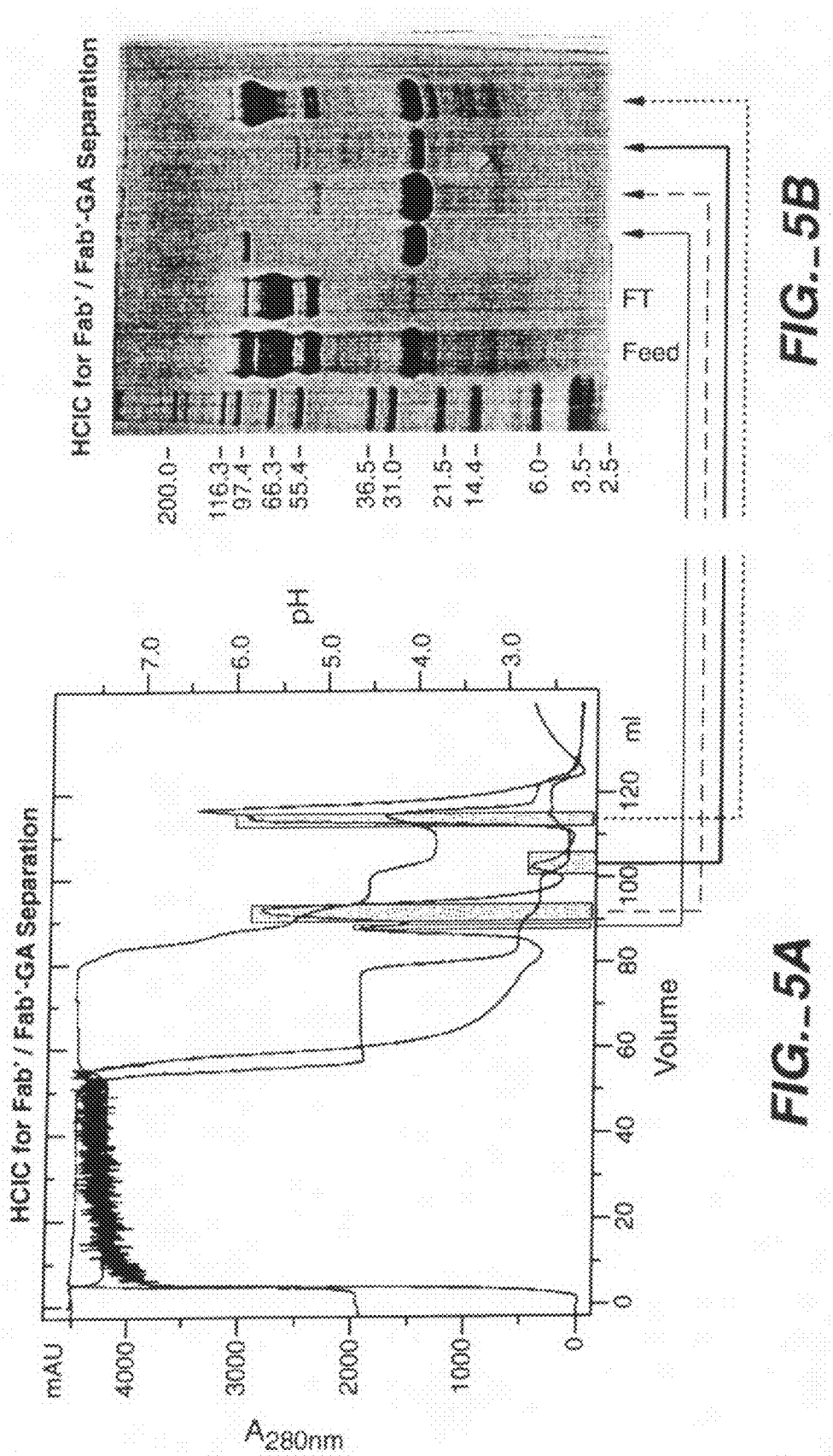
FIG._5B
FIG._5A

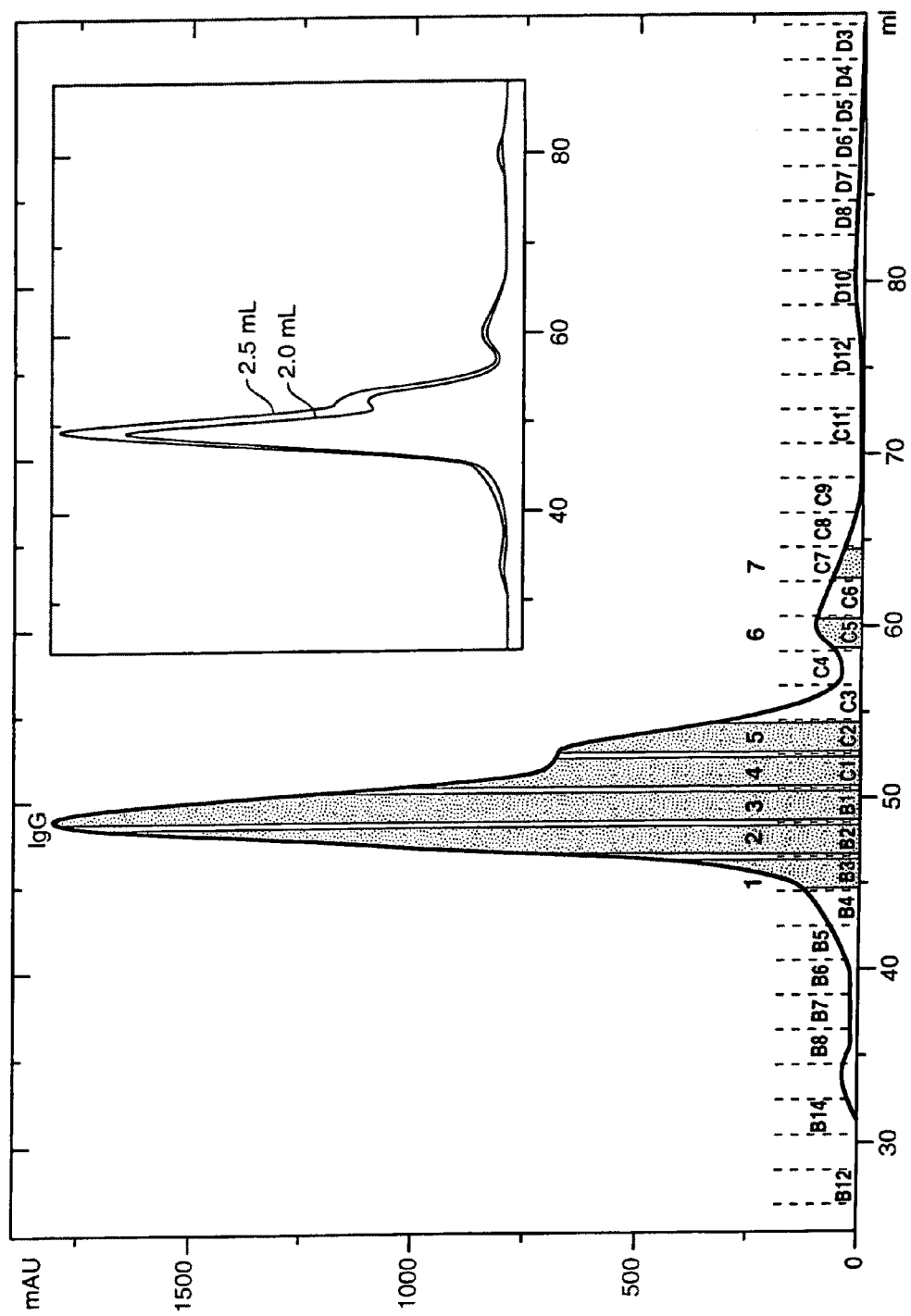
FIG._6A

Reducing SDS-PAGE

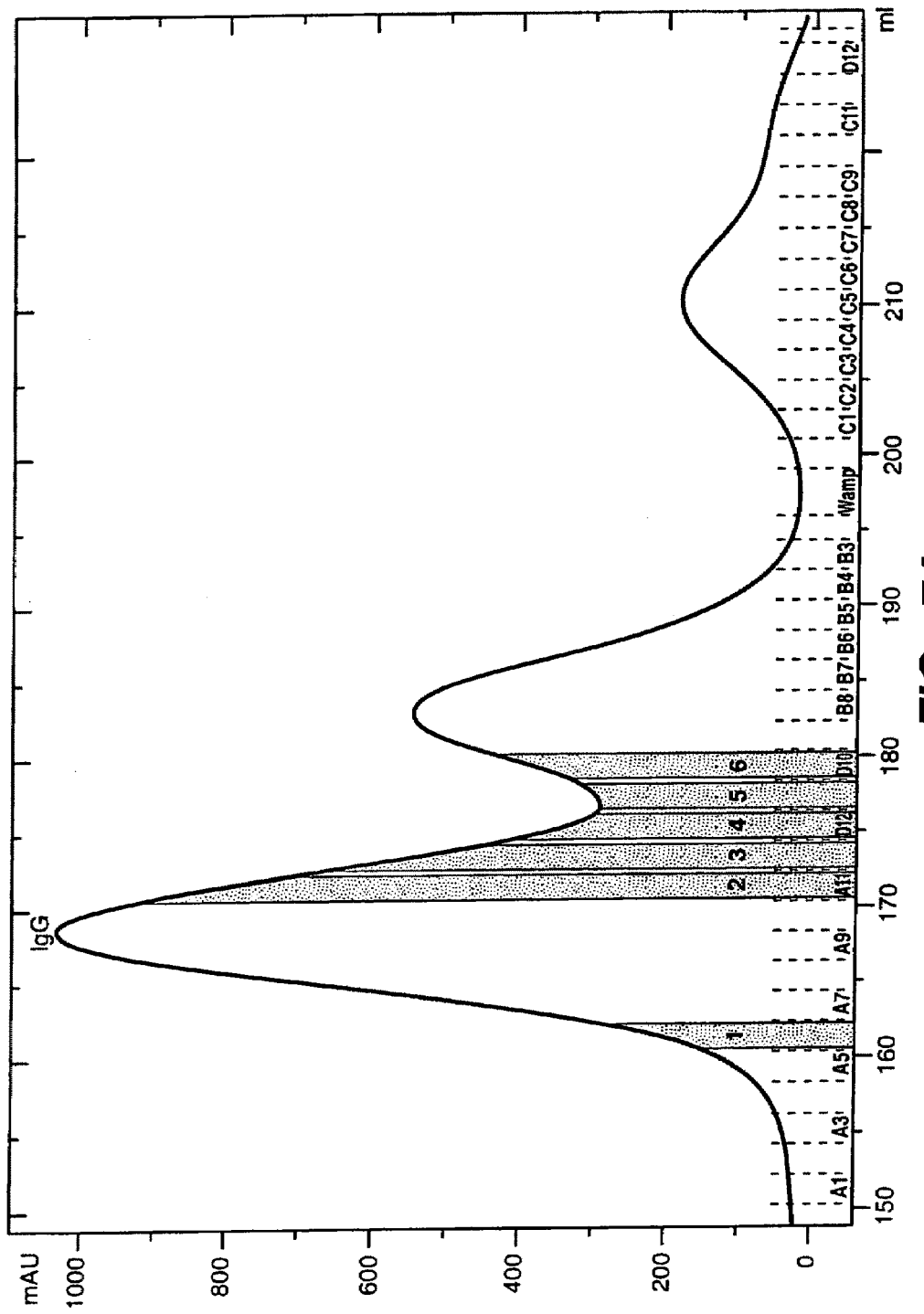
FIG._7A

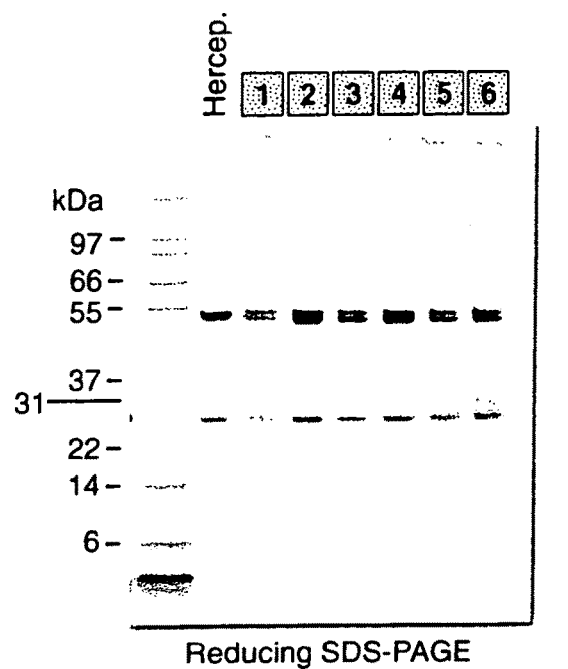
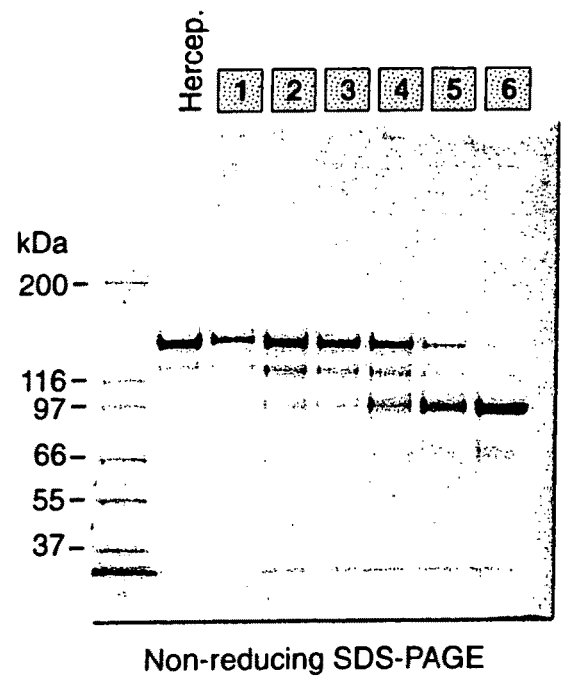
FIG._7B

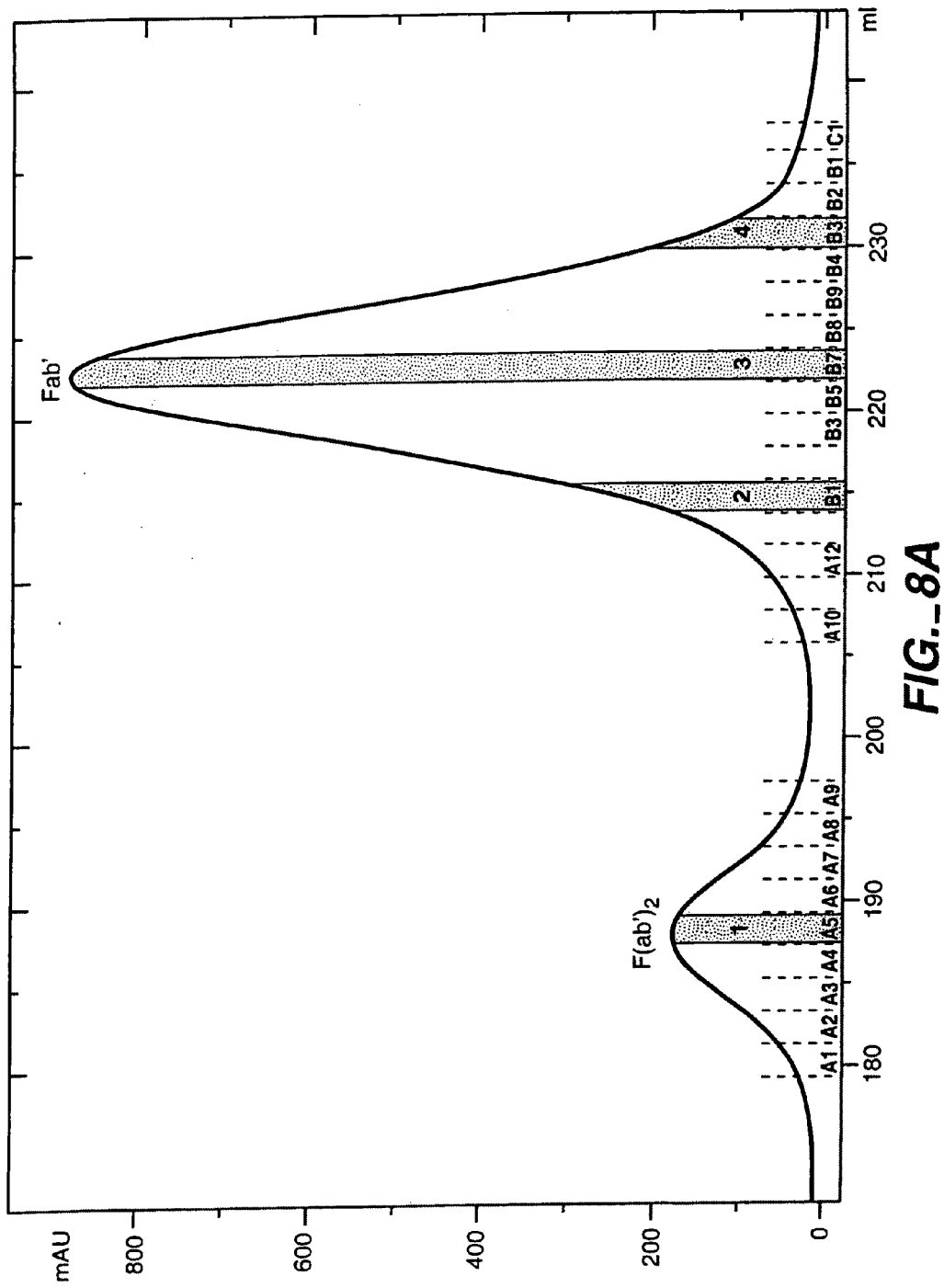
FIG._8A

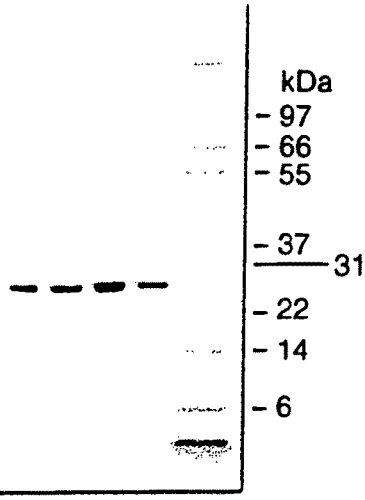
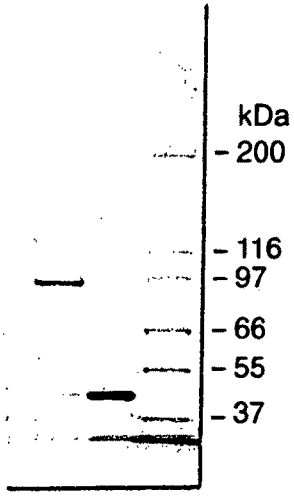
FIG._8B

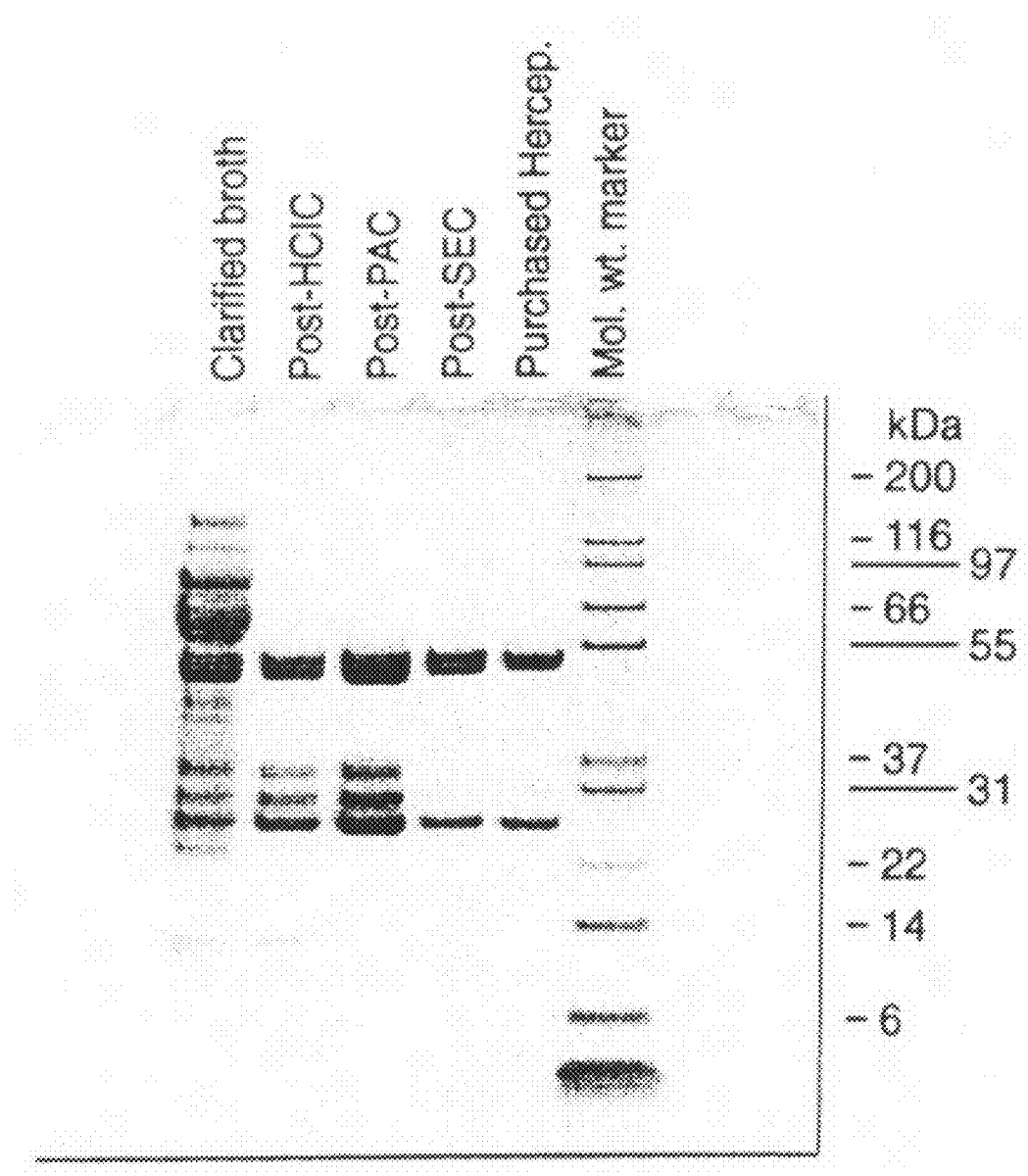
FIG._9

PROTEIN PURIFICATION

CROSS-REFERENCE TO RELATED APPLICATIONS

The present application is a continuation of U.S. Ser. No. 10/663,483, filed on Sep. 15, 2003, issued as U.S. Pat. No. 7,208,585, which is related to applications U.S. Ser. No. 60/373,889, entitled "DNA Sequences, Vectors, and Fusion Polypeptides for Secretion of Antibodies in Filamentous Fungi" filed Apr. 18, 2002, by Ward et al. and U.S. Ser. No. 60/411,540, entitled "DNA Sequences, Vectors, and Fusion Polypeptides for Secretion of Antibodies in Filamentous Fungi", filed Sep. 18, 2002, by Ward et al., and claims priority to U.S. Ser. No. 60/411,537, filed Sep. 18, 2002, entitled "Protein Purification" by Fong et al.

FIELD OF THE INVENTION

This invention relates to a method of purifying a desired protein from a protein mixture comprising its fusion precursor or fusion analog. Specifically, the invention relates to the use of rationally designed liquid chromatography protocol useful in recovering a desired protein from a solution comprising the protein and its fusion analog.

BACKGROUND OF THE INVENTION

Recombinant protein production is well known in the art. Various proteins have been expressed in a variety of host cells. Protein production in filamentous fungi may be enhanced by fusing the desired protein to the signal sequence and/or a secreted polypeptide or portion thereof normally secreted from the host cell. Under most circumstances this will require further processing to release the desired protein from the fusion construct. The separation and purification of a fully cleaved protein of interest from its fusion analog in fermentor broth is a crucial and challenging component of the fungal expression of fusion proteins.

Recently, the production of monoclonal antibodies in filamentous fungi as fusion polypeptides was demonstrated. See co-pending applications U.S. Ser. No. 60/373,889 filed Apr. 18, 2002 and U.S. Ser. No. 60/411,540 filed Sep. 18, 2002, both entitled "DNA Sequences, Vectors, and Fusion Polypeptides for Secretion of Antibodies in Filamentous Fungi", by Ward et al.

The production of the immunoglobulins is as a mixture of fusion proteins and mature (i.e., non-fused) immunoglobulins. This is an unsatisfactory composition for therapeutic purposes. Thus, it is necessary to purify not only the full-length antibodies from the host proteins but also from the various fusion proteins of the mixture. The presence of fusion proteins is an additional challenge for the purification of immunoglobulins from the *Aspergillus* preparation.

A vast amount of literature describing antibody purification has been reported. Liquid chromatography is by far the most commonly used, with two or more chromatographic steps mandatory for therapeutic applications. For example, it has been reported that Protein A chromatography used extensively in the recovery of immunoglobulins from a variety of sources, including cell cultures (Bioseparation and Bioprocessing: A Handbook. Volume 1, chapter 12. Publishers Wiley-VCH, 1998).

Hydrophobic Charge Induction Chromatography (HCIC) has been reported to separate proteins in a one-step elution process. Unfortunately, under current production methods that utilize fusion proteins as described above, the one-step process fails to separate the protein from its fusion analog.

For therapeutic compositions, the challenge is to come up with a rational combination of technologies to remove all relevant impurities from the antibody preparation. Thus, it would be advantageous to have a method of purifying the antibodies, antibody fragments and their respective fusion proteins. In addition, the methods described herein find use for the separation of a protein from its fusion analog.

BRIEF SUMMARY OF THE INVENTION

Provided herein are methods for the purification of a protein of interest from its fusion analog by hydrophobic charge induction chromatography. In one embodiment the method further comprises size exclusion chromatography.

In an aspect of the invention, the protein of interest is a fully assembled mature immunoglobulin. The fusion analog may comprise at least one glucoamylase protein covalently linked to the amino terminus of at least one of the chains in a fully assembled, mature immunoglobulin. Thus, there may be between one and four glucoamylase proteins attached to the mAb or fragment thereof.

In another aspect of the invention, the protein of interest is a fragment of the immunoglobulin.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 is a diagram of a fully assembled, mature monoclonal antibody (A), an antibody fragment (B) and their respective fusion analogs (C and D). Glucoamylase (GA) is represented as large grained ovals. The stippled diamonds on the Fc portion of the mature immunoglobulin represent glycosylation sites. It should be appreciated that the number of GA moieties on the fusion analogs may vary from that shown due to cellular processing. The chains, although produced as fusions, may undergo proteolytic processing, either intracellularly or extracellularly, to remove a GA moiety. An immunoglobulin chain can be covalently attached to one or two other chains through a cysteine linkage. In the case of $F(ab')_2$, two Fab units are attached in this way to form the dimer.

FIG. 2 is a schematic representation of the theorized mechanism of HCIC purification. FIG. 2A is the adsorption of the desired protein onto the resin. FIG. 2B is the elution of bound protein from the resin.

FIG. 3A is the Protein A chromatography elution profile for mAb/mAb-GA. FIG. 3B is a photograph of a SDS-PAGE gel of the peaks indicated in FIG. 3A. FIG. 3B shows the results of SDS-PAGE under reducing conditions (top) and non-reducing conditions (bottom) with Coomassie Brilliant Blue staining of samples that had been purified by Protein A chromatography. The bands observed under reducing conditions were identified as the light chain (25 kDa), non-glycosylated and glycosylated forms of the heavy chain (50 and 53 kDa), glucoamylase-light chain fusion protein (85 kDa) and glucoamylase-heavy chain fusion (116 kDa). Note there was no separation of the immunoglobulin proteins from theirfusion analog. The minor bands above the 25 kDa band are degradation products of the immunoglobulin.

FIG. 4A is the HCIC elution profile of mAb/mAb-GA separation. FIG. 4B is an SDS-PAGE gel run under reducing conditions from various steps during the purification method. In lane 1 is the clarified fermentation broth; the lane is labeled "Feed." In lane 2, is the flow through; the lane is labeled "FT." Lanes 3-5 are eluate collected at the points indicated. Lane 6 is the molecular weight markers. The fusion proteins elute later than the non-fused mAb. Lane 3 has no fusion protein. The bands observed under reducing conditions were identified as the light chain (25 kDa), non-glycosylated and glycosylated forms of the heavy chain (50 and 53 kDa), glucoamylase-light chain fusion protein (85 kDa) and glucoamylase-heavy chain fusion (116 kDa). The minor bands above the 25 kDa band are degradation products of the immunoglobulin.

FIG. 5A is the HCIC elution profile for immunoglobulin fragments, Fab'. FIG. 5B is an SDS-PAGE gel run under reducing conditions from various steps during the purification method. Lane 1 is the molecular weight markers. In lane 2 is the clarified fermentation broth; the lane is labeled "Feed." In lane 3, is the flow through; the lane is labeled "FT." Lanes 4-7 are eluate collected at the points indicated. The band at about 25 kDa was identified as the Fab' fragment. The band at about 55 kDa was identified as the F(ab')$_2$ fragment. The band at about 100 kDa was identified as a Fab'-GA fusion protein. Lanes 5 and 6 have no fusion protein.

FIG. 7 is the size exclusion chromatogram (FIG. 7A) and SDS-PAGE (FIG. 7B) for IgG purification using a 300 mL column and 7.0 mL load volume. The sample had previously undergone HCIC. SDS-PAGE was done under either reducing or non-reducing conditions. The purification method was able to discriminate between mature IgG and incomplete forms.

FIG. 8 is the size exclusion chromatogram (FIG. 8A) and SDS-PAGE (FIG. 8B) for fragment purification using a 300 mL column and 6.5 mL load volume. The sample had previously undergone HCIC. SDS-PAGE was done under either reducing or non-reducing conditions. The purification was effective in separating Fab' from F(ab')$_2$.

FIG. 9 is a photograph of a reducing SDS-PAGE gel. The fermentation broth was run sequentially, in the following order, over chromatography columns: HCIC, PAC then SEC. Lane 1 is the clarified fermentation broth. Lane 2 is the eluate from HCIC run. Lane 3 is the sample after HCIC and Protein A. Protein A was not able to further purify the sample. Lane 4 the sample after HCIC, Protein A and SEC, in that order. Lane 5 is purchased Herceptin™ (a monoclonal antibody). Lane 6 is molecular weight markers.

DETAILED DESCRIPTION

Figure 6B:
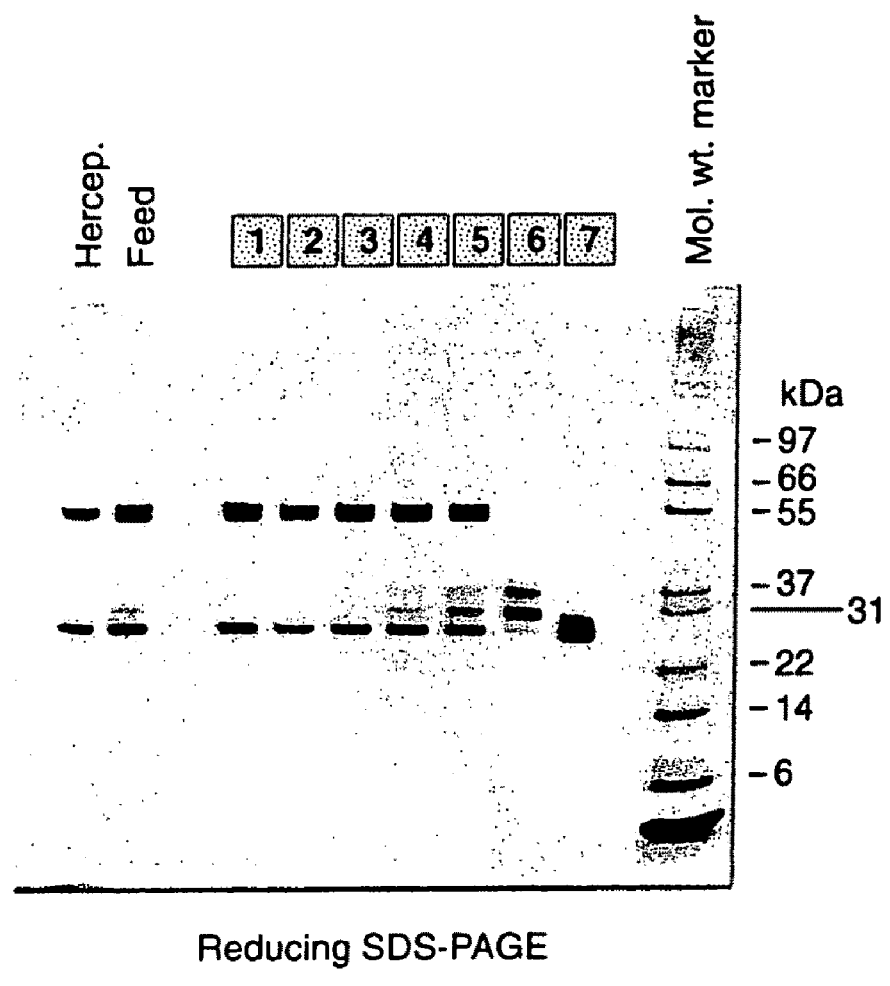
FIG. 6 is the size exclusion chromatogram (FIG. 6A) and SDS-PAGE (FIG. 6B) for IgG purification using a 100 mL column and 2.5 mL load volume. The sample had previously undergone HCIC and is labeled as "Feed." The inset shows the effect that load volume has on resolution. The SDS-PAGE gel was run under reducing conditions. It can be seen that there are no fusion analogs in the samples run on the gel. Fractions 1, 2 and 3 (lanes 4-6, respectively, on the gel) contain a substantially pure immunoglobulin product. Lane 1 is purchased Herceptin™ (a monoclonal antibody available from Genentech, San Francisco, Calif.).

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., Dictionary of Microbiology and Molecular Biology, 2d Ed., John Wiley and Sons, New York (1994), and Hale & Marham, The Harper Collins Dictionary of Biology, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention, which can be had by reference to the specification as a whole. Accordingly, the terms defined immediately below are more fully defined by reference to the specification as a whole.

Definitions

"Antibody" or "immunoglobulin" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, Fundamental Immunology.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The amino terminus of each chain defines a variable domain of about 100 to 110 or more amino acids primarily responsible for antigen recognition. The terms variable light chain (VL) and variable heavy chain (VH) refer to these light and heavy chains respectively. The terms "antibody," "monoclonal antibody" and "immunoglobulin" are used interchangeably herein.

As used herein, the terms "protein of interest" or "polypeptide of interest" refers to a polypeptide or protein in its mature form that is not fused to a secretion enhancing construct. Thus, a "protein of interest" or "polypeptide of interest" refers to the protein to be expressed and secreted by the host cell in a non-fused form. The protein of interest may be any protein that up until now has been considered for expression in prokaryotes. The proteins are not limited by size and thus include peptides, peptide concatamers. In one embodiment, the protein of interest, which is expressed and secreted, include proteins comprising a signal peptide. The protein of interest may be either homologous or heterologous to the host. Thus, a protein of interest may be a secreted polypeptide, particularly an enzyme, which is selected from amylolytic enzymes, proteolytic enzymes, cellulytic enzymes, oxidoreductase enzymes and plant wall degrading enzymes. Examples of these enzymes include amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. The secreted polypeptide may also be a hormone, a growth factor, a receptor, vaccine, antibody or the like. In a preferred embodiment the secreted polypeptide is an immunoglobulin.

A "peptide concatamer" means two or more identical amino acid sequences linked in tandem. The amino acid sequences are usually less than 25 amino acids in length.

As used herein, a "fusion polypeptide" or "fusion protein" or "fusion analog" encodes from its amino-terminus a signal peptide functional as a secretory sequence functional in a host cell, a secreted polypeptide or portion thereof normally secreted from a host cell, a cleavable linker polypeptide and a polypeptide of interest. The fusion protein may be processed by host cell enzymes, e.g., a protease, to yield the protein of interest free from the other protein sequences in the fusion protein. In one embodiment the host cell is a filamentous fungus. The fusion analog may be constructed to facilitate the isolation of the protein of interest without regard to enhanced secretion as the inventive method does not depend on secretion of the protein of interest for its isolation.

As used herein, the terms "fusion analog" or "fusion polypeptide" or "fusion protein" may be used interchangeably.

"Purified" as used herein means that the polypeptide of interest is substantially free from its fusion analog.

The term "substantially free" includes preparations of the polypeptide of interest having less than about 20% (by dry weight) other proteins (i.e., contaminating protein), less than about 10% other proteins, less than about 5% other proteins, or less than about 1% other proteins.

The term "substantially pure" when applied to the proteins or fragments thereof of the present invention means that the proteins are essentially free of other substances to an extent practical and appropriate for their intended use. In particular, the proteins are sufficiently pure and are sufficiently free from other biological constituents of the host cells so as to be useful in, for example, protein sequencing, or producing pharmaceutical preparations.

The term "HCIC resin" means a chromatographic means having a solid support matrix and a selected ionizable ligand. See U.S. Pat. No. 5,652,348. Suitable solid support matrices include, but are not limited to, those chromatographic solid support matrices described in U.S. Pat. No. 5,652,348, membrane adsorber (for example, surface modified hydrophilic polyethersulfone or cellulose), and soluble polymer adsorbers. Examples of soluble polymer adsorbers include synthetic, as well as naturally occurring, polymers capable of modification with multiple ligands. In particular, it is contemplated that environmentally sensitive polymers [e.g. poly(N-isopropylacrylamide), poly(methacrylic acid), Eudragit, galactomannan] will find use with the inventive method. These polymers precipitate in response to a stimulus such as temperature, pH, or ionic strength.

"Clarified Broth" means a fermentation broth that has had cells and cellular debris and particulate matter removed.

Host Cells and Culture Conditions

Host cells, preferably eukaryotic cells, useful in the present invention are any that may be transformed to allow the expression and secretion of proteins of interest and fusion analogs thereof. The host cells may be mammalian cells, yeast, filamentous fungi or bacteria. Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*. Various bacteria include *Escherichia* and *Bacillus*. Yeasts belonging to the genera *Saccharomyces, Kiuyveromyces, Hansenula*, or *Pichia* would find use as an appropriate host cell.

Examples of usable host organisms include bacteria, e.g., *Escherichia coli* MC1061, derivatives of *Bacillus subtilis* BRB1 (Sibakov. et al., Eur. J. Biochem., 145:567-572, 1984), *Staphylococcus aureus* SAI123 (Lordanescu, J. Bacteriol, 12:597-601, 1975) or *Streptococcus lividans* (Hopwood et al., Genetic Manipulation of *Streptomyces*. A Laboratory Manual, The John Innes Foundation, Norwich 1985); yeasts, e.g., *Saccharomyces cerevisiae* AH 22 (Mellor et al., Gene, 24:1-14, 1983) and *Schizosaccharomyces pombe*; filamentous fungi, e.g., *Aspergillus nidulans, Aspergillus awamori* (Ward, Proc, Embo-Alko Workshop on Molecular Biology of Filamentous Fungi, Helsinki, pp. 119.128,1989), *Trichoderma reesei* (Penttilâ et al., Gene 61:155-164, 1987; Harkki et al, BioTechnology, 7:596-603, 1989). Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (HA4-II-E; ATCC CRL1548) SV40-transformed monkey kidney cells (COS-1; ATCC CRL 1650) and murine embryonic cells (NIH-3T3; ATCC CRL 1658). Preferably, the mammalian host cells are NIH-3T3 cells. The foregoing being illustrative but not limitative of the many possible host organisms known in the art. In principle, all hosts capable of secretion can be used whether prokaryotic or eukaryotic.

Cells expressing the protein of interest and/or their fusion analogs are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the protein of interest and/or their fusion analogs are achieved.

Preferred culture conditions for a given cell line may be found in the scientific literature and/or from the source of the cell line such as the American Type Culture Collection (ATCC; P.O. Box 1549, Manassas, Va. 20108). Typically, after cell growth has been established, the cells are exposed to conditions effective to cause or inhibit the expression of the protein of interest and/or their fusion analogs.

Transformation and Expression of Fusion Polypeptides

To the extent that this invention depends on the production of fusion proteins, it relies on routine techniques in the field of recombinant genetics. Basic texts disclosing the general methods of use in this invention include Sambrook et al., *Molecular Cloning, A Laboratory Manual* (2nd ed. 1989); Kniegler, *Gene Transfer and Expression: A Laboratory Manual* (1990); and Ausubel et al., eds., *Current Protocols in Molecular Biology* (1994)).

Production of fusion proteins can be accomplished by use of the methods disclosed in, for example, U.S. Pat. Nos. 5,411,873, 5,429,950, and 5,679,543. Other methods are well known in the art.

Basically, a heterologous gene encoding a fusion protein is operably linked to a promoter sequence functional in the host cell. This promoter-gene unit is then typically cloned into intermediate vectors before transformation into the host cells for replication and/or expression. These intermediate vectors are typically prokaryotic vectors, e.g., plasmids, or shuttle vectors.

To obtain high level expression of a cloned gene, the heterologous gene encoding a fusion protein is preferably positioned about the same distance from the promoter as is in the naturally occurring gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The choice of promoter used in the genetic construct is within the knowledge of one skilled in the art.

In addition to a promoter sequence, the expression cassette should also contain a transcription termination region downstream of the structural gene to provide for efficient termination. The termination region may be obtained from the same gene as the promoter sequence or may be obtained from different genes, also within the knowledge of one skilled in the art.

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

The methods of transformation used may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce host cells that express large quantities of the heterologous fusion protein. Some of the published methods for the introduction of DNA constructs into cells include calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene encoding the fusion polypeptide.

After the expression vector is introduced into the cells, the transfected cells are cultured under conditions favoring expression of genes under control of cellulase gene promoter sequences. Large batches of transformed cells can be cultured as described above. Finally, product is recovered from the culture using techniques of the present invention.

Protein Separations

Once the protein of interest is expressed and, optionally, secreted, recovery of the protein of interest may be necessary. The present invention provides methods of separating a protein of interest from its fusion analog. It is specifically contemplated that the methods described herein are useful for the separation of monoclonal antibodies from their fusion analog.

The method of the invention can be applied to purification of a protein of interest obtained from an aqueous protein solution, in particular to purification of a protein of interest, such as an enzyme or immunoglobulin, from a fermentation broth.

The method of the invention may be applied to an untreated fermentation broth or to a fermentation broth that has first been subjected to, e.g., a pH adjustment, an ionic strength adjustment, a temperature adjustment, a water dilution and/or one or more solid/liquid separatory techniques such as flocculation, centrifugation, filtration or micro filtration.

When the expressed polypeptide of interest is secreted, the polypeptide may be purified from the growth media. Preferably the expression host cells are removed from the media before purification of the polypeptide (e.g. by centrifugation).

When the expressed recombinant polypeptide of interest is not secreted from the host cell, the host cell is preferably disrupted and the polypeptide released into an aqueous "extract" which is the first stage of purification. Preferably the expression host cells are collected from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

It is specifically contemplated that $IgG_1$ monoclonal antibody and antibody fragments may be purified from clarified broth using a combination of hydrophobic charge induction chromatography (HCIC), Protein A affinity chromatography (PAC), and size exclusion chromatography (SEC). The Protein A chromatography is optional. Each of these methods were performed with the aid of a high performance liquid chromatographic system (AKTAT™explorer 10, Amersham Biosciences). Purified IgG, Fab', and $F(ab')_2$ could be obtained by sequentially performing HCIC and SEC. HCIC provided an ability to separate antibody molecules from the broth and from glucoamylase-fusion constructs of the antibody. SEC served as a polishing step to mainly remove incomplete antibody molecules, antibody fragments or to separate Fab' from $F(ab')_2$, as the case may be. For greater purity, PAC could be included either before or after HCIC.

However, as will be appreciated, PAC could not separate antibody from their corresponding glucoamylase-fusion constructs.

Hydrophobic Charge Induction Chromatography

Hydrophobic Charge Induction Chromatography (HCIC), developed by GCOR and Massey University, has traditionally been used for protein separation. HCIC is based on the pH-dependent behavior of the ionizable, dual-mode ligands. Adsorption is based on mild hydrophobic interaction. Desorption is based on charge repulsion achieved by altering the mobile phase pH. See FIGS. 2A and 2B. See also, for example, U.S. Pat. No. 5,652,348.

By making the appropriate selection for each of the components of the resin, the hydrophobic character of the resin at the pH of target compound binding thereto can be rationally selected to enhance the binding efficiency and/or increase binding specificity of the target compound to the resin. Likewise, the hydrophilic and/or electrostatic (ionic) character of the resin at the pH of target compound desorption from the resin can be rationally selected so as to ensure proper desorption of the target compound from the resin. Depending on the type of HCIC resin used elution may require a pH gradient from low to high pH or high to low pH. Thus, the inventive method allows for the purification of any protein when the appropriate HCIC resin is used in combination with an appropriate pH gradient, i.e., from acid to alkali or vice versa. An example of a commercially available HCIC resin is MEP HyperCel™ (Ciphergen, Fremont, Calif.).

The MEP HyperCel™ sorbent is a high capacity, highly selective chromatography material specially designed for the capture and purification of monoclonal and polyclonal antibodies from the extracellular milieu. It provides an extremely effective antibody purification method from ascites, defined growth media and serum. However, it has not previously been reported to discriminate between the antibody and its fusion analog.

A. Sample Preparation

The sample containing the protein of interest may be clarified using any appropriate means known to one skilled in the art. Exemplary methods include centrifugation and filtration to remove cell debris. However, it should be appreciated that clarification is not a required step.

To the clarified broth is added an appropriate buffer in an amount necessary to adjust the sample to the pH appropriate for the resin used. A concentrated stock buffer may be used to decrease the amount of buffer required to adjust the pH. Thus, for example, if a 10× stock loading solution is available then for every 9 parts of sample 1 part of the 10× stock buffer is added. An exemplary buffer (final concentrations are given) is 50 mM Tris/HCl, 200 mM NaCl, pH 8.2. Considerations in choosing a buffer are desired product stability in buffer, buffer effectiveness for target operating range; buffer cost; and amenability to subsequent steps in purification.

The aqueous medium may include a buffer and/or a salt to enhance binding efficiencies to the resin. However, one of the advantages of HCIC is that binding of the protein of interest can be achieved at both high and low ionic strength and, accordingly, the addition of salt to the aqueous medium may or may not be necessary. Suitable salts are those conventionally employed in chromatography and include, by way of example, the lithium, sodium, potassium, ammonium, calcium and magnesium salts of chloride, sulfate, phosphate and acetate. Preferably, sodium chloride is employed because it is effective, inexpensive and safe.

B. Pre-Equilibration

The HCIC resin is pre-equilibrated with a suitable buffer. This is termed an "Equilibration Buffer" and may/should be the same as the loading buffer used in the sample preparation. The sample containing the protein of interest is then contacted with the HCIC resin for a time sufficient to allow binding of the protein of interest to the HCIC resin. An example of an appropriate Loading/Equilibration buffer is: 50 mM Tris-HCl, 200 mM NaCl, pH 8.2.

It will be appreciated by one skilled in the art that the protein solution may be applied to any HCIC resin that has been pre-equilibrated. This can be done in a batch process or in a column based process. The columns may be, for example, a packed column, an axial flow column, a radial flow column, an expanded bed column and the like. This can also be done with other support matrices as provided for above.

C. Wash

The column is washed with a sufficient amount of an appropriate buffer to remove any unbound protein or other contaminants. An appropriate buffer is, for example, the loading buffer. Unbound contaminants were washed out with 1-10 column volumes of the appropriate buffer. If desired, more than one wash buffer may be used to enhance the removal of unbound contaminants, e.g, a wash with the load buffer followed by a wash with a lower ionic strength load buffer.

D. Elution by pH Steps

The peptide of interest is eluted from the column by a pH gradient. In some embodiments, the pH gradient begins at a pH of about 8 and ends at a pH of about 2.5. In other embodiments, the pH gradient begins at a pH of about 2.5 and ends at a pH of about 8. In further embodiments, the pH gradient is a step pH gradient and comprises between two and six steps. The rate at which the desired protein is desorbed from the resin is determined by hydrophobic and charge characteristics of the protein of interest. The proteins will elute in order of increasing hydrophobicity. To a limited extent, the flow rate will affect the elution profile with faster flow rates giving broader peaks. Appropriate buffers are, for example, Elution Buffer #1: 100 mM Sodium Acetate, pH 5.6; Elution Buffer #2: 100 mM Sodium Acetate, pH 4.75; Elution Buffer #3: 100 mM Sodium Acetate, pH 4.00; and Elution Buffer #4: 100 mM Sodium Citrate, pH 2.5.

E. Regeneration

As a final, optional, step the column may be regenerated by conventional methods, i.e., with an appropriate acid or base, as suggested by the manufacturer.

Affinity Chromatography

Affinity Chromatography is based on an affinity ligand, covalently linked to an inert chromatography matrix, that binds to a specific binding site on the target molecule, e.g., a protein of interest. Under suitable binding conditions this affinity matrix will bind molecules according to its specificity only. All other sample components will pass through the medium unabsorbed. After a wash step the adsorbed molecules are released and eluted by changing the conditions towards dissociation or by adding an excess of a substance that displaces the target molecule from the affinity ligand.

The basic steps for affinity chromatography are as follows. First, the column is conditioned to promote adsorption of the target molecule by equilibrating it with binding buffer. Second, The sample is applied under binding conditions. The target molecule binds specifically to the affinity ligands, while all other sample components are washed through. And, lastly, the target molecule is desorbed and eluted by switching to elution buffer.

Finding a suitable ligand in affinity chromatography is not restricted to just specificity, but concerns also the binding strength and the kinetics of the ligand-target molecule reaction. Ideally the binding should be strong enough to avoid leakage during the sample application and wash phase, while the target molecule should be completely released during the elution phase.

Thus, the important considerations in affinity chromatography are the affinity ligand, and the binding conditions.

Protein A is a highly stable surface receptor produced by *Staphylococcus aureus*, which is capable of binding the Fc portion of immunoglobulins, especially IgGs, from a large number of species (Boyle and Reis, 1987).

Protein A will bind the Fc portion of human IgG subclasses, IgM, IgA and IgE; and mouse IgG1 (weakly), IgG2a and IgG2b. Protein A also binds IgGs from other laboratory and domestic animals, including monkey, rabbit, pig, guinea pig, dog and cat. Protein A may be immobilized onto a solid support to facilitate the purification and recovery of either polyclonal or monoclonal immunoglobulins. Thus, it has found use in the purification of immunoglobulins. In fact, Protein A chromatography media is the well-established industrial standard for the purification of monoclonal antibodies. However, Protein A affinity-chromatography media is expensive. In addition, it was surprising to find that Protein A did not demonstrate preferential binding for monoclonal antibodies over their fusion analog.

Size Exclusion Chromatography

In most antibody preparations there is a possibility that IgG aggregates and/or dimers are present. It is therefore advantageous to include a gel filtration polishing step, despite the high degree of purity that may be achieved using the inventive method described herein. The polishing step removes low or trace levels of contaminants.

Size exclusion chromatography (SEC), also called gel-filtration or gel-permeation chromatography (GPC), uses porous particles to separate molecules of different sizes. It is generally used to separate biological molecules, and to determine molecular weights and molecular weight distributions of polymers, e.g., proteins. Molecules that are smaller than the pore size can enter the particles and therefore have a longer path and longer transit time than larger molecules that cannot enter the particles.

SEC is a very mild separation method because any desirable buffer can be used.

The porosity of the particles can be adjusted to exclude all molecules above a certain size. Sephadex and sepharose are trade names for gels that are available commercially in a broad range of porosities.

For SEC, packing of the column is critical. The column dimensions may range from 600 mm×16 mm to 1000 mm×50 mm. The volume of the loaded sample should not exceed 5% of the column volume for preparative runs and 1% for analytical applications.

The flow rate of the elution buffer significantly affects the resolution. The manufacturers recommended flow rates, which depend on the column diameter, should not be increased. In general, running the column at a low flow rate results in higher resolution, but diffusion may occur, when the flow rate is too low.

Exemplary conditions for SEC are given below. Size exclusion chromatography may be run on columns ranging from 10 mL to 2500 L. Columns were packed with Superdex 200 Prep Grade media (Amersham Biosciences) or other media that provides similar separation in the desired molecular weight range. Sample loading sizes were 0.5-5% of the column volume. Flow rates were on the order of 10 cm/h. The flow rate can range between 5 cm/h and 20 cm/hr. The buffer was 20 mM sodium acetate, pH 5.5 containing 136 mM sodium chloride or any other buffer in which the protein is stable. Sometimes the addition of 0.1 M sodium dodecyl sulfate is necessary to solubilize certain proteins. Proteins exiting the column were detected by absorbance of ultraviolet light. For protein, detection is typically performed at 280 nm.

Selection of a particular column and solvent, i.e., buffer, is a matter of routine design. See, for example, Affinity Chromatography: Principles & Methods, Pharmacia LKB Biotechnology, Uppsala, Sweden, 1988; Hunt, G. J.; Size Exclusion Chromatography; Chapman & Hall, New York, 1979; Yau, W. W.; J. J. Kirkland; D. D. Bly; Modern Size Exclusion Chromatography, J. Wiley & Sons, New York, 1979; and Dublin, P. L.; Aqueous Size-Exclusion Chromatography; Journal of Chromatography Lib. 40, Elsevier, 1988.

The ability to separate a protein of interest from incomplete fragments thereof and its fusion analogs is crucial to obtaining a substantially pure composition of the protein of interest. The inventive methods described herein provide such compositions.

Materials

The following HCIC buffers and solutions were used in the following examples
Loading/Equilibration Buffer: 50 mM Tris-HCl, 200 mM NaCl, pH 8.2;
Elution Buffer #1: 100 mM Sodium Acetate, pH 5.6;
Elution Buffer #2: 100 mM Sodium Acetate, pH 4.75;
Elution Buffer #3: 100 mM Sodium Acetate, pH 4.00;
Elution Buffer #4: 100 mM Sodium Citrate, pH 2.5;
Cleaning Solution: 0.5M NaOH;
Column Storage Buffer: 1M NaCl in 20% Ethanol; and
Neutralizing buffer: 1M Tris-HCl, pH 8.5-9.5.

The following PAC buffers and solutions were used in the following examples:
Loading/Equilibration Buffer: 25 mM Tris-HCl, pH 7.7;
Washing Buffer: 25 mM Tris-HCl, 500 mM NaCl, pH 7.7;
Elution Buffer: 100 mM Sodium Citrate, pH 2.5;
Column Storage Buffer: 1M NaCl in 20% Ethanol; and
Neutralizing buffer: 1M Tris-HCl, pH 8.5-9.5.

The following SEC buffers and solutions were used in the following examples:
SEC Buffer: 20 mM sodium acetate, 136 mM NaCl, and pH 5.5; and
Column Storage Buffer: 0.01M NaOH.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); kDa (kilodaltons); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); SDS-PAGE (Sodium dodecylsulfate-polyacrylamide gel electrophoresis); CV (column volume); MW (molecular weight).

EXAMPLES

The following examples are offered to illustrate, but not to limit the claimed invention.

Example 1

Fermentation Broth Clarification

Fungal cells were transformed and cultured according to the methods described in co-pending applications U.S. Ser. No. 60/373,889, entitled "DNA Sequences, Vectors, and Fusion Polypeptides for Secretion of Antibodies in Filamentous Fungi" filed Apr. 18, 2002, by Ward et al. and U.S. Ser. No. 60/411,540, entitled "DNA Sequences, Vectors, and Fusion Polypeptides for Secretion of Antibodies in Filamentous Fungi", filed Sep. 18, 2002, by Ward et al., both of which are incorporated by reference in their entirety. Briefly, fungal cells that had previously been transformed with heterologous DNA encoding an immunoglobulin were grown in 50 ml of production medium called Promosoy special. This medium had the following components: 70 g/l sodium citrate, 15 g/l $(NH_4)_2 SO_4$, 1 g/l $NaH_2PO_4.H_2O$, 1 g/l $MgSO_4$, 1 ml Tween 80, pH to 6.2 with NaOH, 2 ml/l Mazu DF60-P, 45 g/l Promosoy 100 (Central Soya, Fort Wayne, Ind.), 120 g/l maltose. The production media flasks were incubated at 30° C., 200 rpm for 5 days. After 5 days, the fungal cells were removed from fermentation broth by vacuum filtration. A porous cellulose pad of roughly 8-micrometer pore size (K900, Sietz) was placed atop the perforated surface of a Buchner funnel. While vacuum was applied to the funnel, an aqueous slurry of diatomaceous earth (FW12, Eagle Picher) was poured onto the pad to generate a packed-bed filter of approximately 5-millimeter thickness. Whole broth was then poured directly onto the filter bed. At all times, the bed was kept moist to prevent cracking. Clogging was reduced by including diatomaceous earth in the broth (2% FW12) and by gently scraping the surface of the bed with a spatula during filtration.

The filtered broth was concentrated approximately sevenfold by tangential ultrafiltration. Using a circulating pump, the broth was pressurized and flowed across a membrane made of regenerated cellulose with a 30,000 molecular weight cutoff (Prep/Scale™ TFF, Millipore) and concentrated to 0.8-1 L.

To further remove particulates, the concentrate was centrifuged at 25,000 times gravity for 15 minutes, and the supernatant was filtered through a series of membranes, with each membrane having a smaller pore size than the previous, ending with 0.2-micrometer pore size. This clarified broth may be stored frozen until further use or used immediately.

Example 2

Protein-A Chromatography for Antibodies and Antibody Fragments Purification

Protein-A Chromatography (PAC) was performed using a 5 mL column containing Protein A Ceramic HypderD® F. media (Ciphergen Biosystems). The column was equilibrated with 25 mM Tris and pH 7.7 buffer. A sample that had been adjusted to pH 7.7 was then loaded onto the column at 45 cm/h. The column washed with 6 CV of 25 mM Tris, 500 mM NaCl, and pH 7.7 buffer. Antibody was eluted with 4.5 CV of 100 mM sodium citrate and pH 2.5 buffer flowing at 150 cm/h. Eluate containing antibody was collected and immediately neutralized with 1M Tris and pH 8.2 buffer. The chromatogram is shown in FIG. 3A.

Aliquots from the collected fractions were assessed on SDS-PAGE (FIG. 3B). SDS-PAGE was done according to manufacturer's instruction. Gels, molecular weight standards, and buffers were purchased from Invitrogen in Carlsbad, Calif. The gel used was NuPAGE® 4-12% Bis-Tris gel with MES running buffer. Samples were reduced with 1% beta-mercaptoethanol (BME). Molecular weight standard was Mark 12 also from Invitrogen. For non-reducing conditions, BME was omitted and MOPS running buffer was used instead of MES. In all other examples, non-reducing gels were done in the absence of BME on NuPAGE® 3-8% Tris-acetate gels with Tris-acetate running buffer.

FIG. 3B shows that Protein A was not able to discriminate between monoclonal antibodies (mAb) and their fusion analogs (mAb-GA). Both species were captured and co-eluted in concentrated form. Furthermore, Protein A was not able to further purify the mAb if it was performed after HCIC. See FIG. 9.

Example 3 mAb/mAb-GA Purification using HCIC

Firstly, the fermentation broth was clarified as in Example 1. Basically, fungal cells were removed from culture broth by filtration through a cellulose pad as describe in Example 1. The filtered broth was concentrated approximately sevenfold by tangential ultrafiltration. Using a circulating pump, the broth was pressurized and flowed across a membrane made of regenerated cellulose with a 30,000 molecular weight cutoff (Prep/Scale™ TFF, Millipore). To remove particulates, the concentrate was centrifuged at 25,000 times gravity for 15 minutes, and the supernatant was filtered through a series of membranes, with each membrane having a smaller pore size than the previous, ending with 0.2-micrometer pore size.

IgG1 was purified from supernatant using hydrophobic charge induction chromatography (HCIC)(FIG. 4A). This was performed with the aid of a high performance liquid chromatographic system (AKTAT™explorer 10, Amersham Biosciences) on a 4.5 mL HCIC-MEP Column. HCIC provided an ability to separate antibody molecules from other supernatant proteins and from glucoamylase-fusion proteins. It was carried out using a column containing MEP Hyper-Cel® (Ciphergen Biosystems) media. The column was equilibrated with 50 mM Tris, 200 mM NaCl, and pH 8.2 buffer. Supernatant, adjusted to pH 8.2, was applied to the column at a linear flow rate of 100 cm/h. After washing with five column volumes (5 CV) of equilibration buffer (50 mM Tris-HCl, 200 mM NaCl, pH 8.2), bound molecules were eluted by incrementally decreasing the pH. Two CV of each of the following buffers were delivered to the column at 200 cm/h, in the order listed: 100 mM sodium acetate, pH 5.6; 100 mM sodium acetate, pH 4.75; 100 mM sodium acetate, pH 4.0; and 100 mM sodium citrate, pH 2.5. Free IgG1 eluted within the pH range 4.5-5.5 and was immediately neutralized with 1 M Tris and pH 8.2 buffer. The purity of the antibody exiting the column was assessed by SDS-PAGE. See FIG. 4B.

Example 4

Fab'/Fab'-GA Purification using HCIC

The inventive method was also shown to separate the Fab' from its fusion analog, i.e., Fab'-GA, using the protocol as described in Example 3.

Free Fab' eluted within the pH range 4.5-5.5 and was immediately neutralized with 1 M Tris and pH 8.2 buffer (FIG. 5A). The purity of the antibody exiting the column was assessed by SDS-PAGE. See FIG. 5.

Example 5

SEC Purification

SEC was done after HCIC to remove incomplete forms of the antibody and resulted in monoclonal antibody substantially free of contaminants.

A HiLoad™ 26/60 column with Superdex 200™ Prep Grade media (Amersham Biosciences) was used for SEC. The flow rate was kept at 17 cm/h. After equilibrating the column with 20 mM sodium acetate, 136 mM NaCl, and pH 5.5 buffer, a 6.5-mL sample was driven through the column with 1 CV of equilibration buffer. Two column sizes were investigated, 100 mL and 300 mL.

Initial evaluation of the media using the 100 mL column showed adequate purification of immunoglobulin (FIG. 6). To increase throughput, a 300 mL column was evaluated. With a 20% increase in column length, the 300 mL column provided an improvement in the separation of the immunoglobulin from a major impurity, an apparent incomplete form of the immunoglobulin. See FIG. 7. Fab' monomer and dimer, i.e., F(ab')$_2$, were also separated by the method. See FIG. 8.

The substantially pure monoclonal antibody thus obtained retained biological activity (data not shown) as measured and described in co-pending applications U.S. Ser. No. 60/373,889, entitled "DNA Sequences, Vectors, and Fusion Polypeptides for Secretion of Antibodies in Filamentous Fungi" filed Apr. 18, 2002, by Ward et al. and U.S. Ser. No. 60/411,540, entitled "DNA Sequences, Vectors, and Fusion Polypeptides for Secretion of Antibodies in Filamentous Fungi", filed Sep. 18, 2002, by Ward et al. Thus, the present inventive protein purification method provides monoclonal antibody composition substantially free of contaminants.

It is understood that the examples and embodiments described herein are for illustrative purposes only and that various modifications or changes in light thereof will be suggested to persons skilled in the art and are to be included within the spirit and purview of this application. All publications, patents, and patent applications cited herein are hereby incorporated by reference in their entirety for all purposes.

What is claimed is:

1. A method of purifying a protein of interest from its fusion analog, said method comprising:
   a. Obtaining a protein solution comprising the protein of interest and its fusion analog;
   b. Adjusting the pH and/or ionic strength of the protein solution with an appropriate buffer for the Hydrophobic Charge Induction Chromatography (HCIC) resin used in step c;
   c. Contacting the protein solution with an HCIC resin for a time sufficient to allow binding of the protein of interest and its fusion analog to the resin, wherein said binding is performed in a batch process;
   d. Washing the HCIC resin with an appropriate buffer; and
   e. Eluting the protein of interest from the HCIC resin by a pH gradient;
      wherein said protein of interest is substantially free of its fusion analog.

2. The method of claim 1 wherein the protein solution is a fermentation broth.

3. The method of claim 2 wherein the broth is clarified.

4. The method of claim 1 wherein the protein of interest is secreted.

5. The method of claim 1 wherein the protein of interest is a peptide concatamer.

6. The method of claim 1 wherein the protein of interest is an immunoglobulin or fragment thereof.

7. The method of claim 6 wherein the immunoglobulin is a monoclonal antibody.

8. The method of claim 6 wherein the immunoglobulin is a F(ab')$_2$ fragment.

9. The method of claim 6 wherein the immunoglobulin is a Fab' fragment.

10. The method of claim 1 wherein the protein of interest is an enzyme.

11. The method of claim 1 wherein the fusion analog thereof comprises at least one glucoamylase protein covalently linked to the amino terminus of said protein of interest.

12. The method of claim 11 wherein there may be between one and four glucoamylase proteins attached to said immunoglobulin.

13. The method of claim 1 wherein the protein of interest is a fragment of an immunoglobulin.

14. The method of claim 1 wherein the pH gradient begins at a pH of about 8 and ends at a pH of about 2.5.

15. The method of claim 1 wherein the pH gradient begins at a pH of about 2.5 and ends at a pH of about 8.

16. The method of claim 1 wherein the pH gradient comprises a step pH gradient.

17. The method of claim 16 wherein the step pH gradient comprises between two and six steps.

18. The method of claim 1 further comprising size exclusion chromatography.

19. The method of claim 1 further comprising protein A chromatography.

20. The method of claim 1 in which elution is done in a batch process.

21. The method of claim 1, wherein said pH gradient is from acidic to alkaline pH.

22. The method of claim 1, wherein said pH gradient is from alkaline to acidic pH.

23. The method of claim 1, wherein said protein of interest is an expressed recombinant polypeptide that is not secreted from a host cell, wherein said host cell is disrupted to release said polypeptide.

24. The method of claim 1, wherein said protein of interest is an expressed recombinant polypeptide that is secreted from a host cell.

25. The method of claim 1, wherein said washing and eluting are performed in a column.

26. A method of purifying a protein of interest from its fusion analog, said method comprising:
   a. Obtaining a protein solution comprising the protein of interest and its fusion analog;
   b. Adjusting the pH and/or ionic strength of the protein solution with an appropriate buffer for the HCIC resin used in step c;
   c. Contacting the protein solution with an HCIC resin column for a time sufficient to allow binding of the protein of interest and its fusion analog to the resin;
   d. Washing the HCIC resin with an appropriate buffer; and
   Eluting the protein of interest from the HCIC resin by a pH gradient;
      wherein said protein of interest is substantially free of its fusion analog,
      wherein the pH gradient begins at a pH of about 8.2 and ends at a pH of about 2.5.

* * * * *